(12) United States Patent
Sampson et al.

(10) Patent No.: US 6,981,980 B2
(45) Date of Patent: Jan. 3, 2006

(54) SELF-INFLATING INTRAGASTRIC VOLUME-OCCUPYING DEVICE

(75) Inventors: Douglas C. Sampson, Palm City, FL (US); Michael Zanakis, Stuart, FL (US)

(73) Assignee: Phagia Technology, Stuart, FL (US)

( * ) Notice: Subject to any disclaimer, the term of this patent is extended or adjusted under 35 U.S.C. 154(b) by 38 days.

(21) Appl. No.: 10/390,902

(22) Filed: Mar. 19, 2003

(65) Prior Publication Data

US 2004/0186502 A1   Sep. 23, 2004

(51) Int. Cl.
  *A61M 29/02*   (2006.01)
(52) U.S. Cl. .................................................... 606/192
(58) Field of Classification Search ............... 606/192, 606/195; 604/97.01
  See application file for complete search history.

(56) References Cited

U.S. PATENT DOCUMENTS

| | | | |
|---|---|---|---|
| 4,133,315 A | 1/1979 | Berman et al. | |
| 4,234,454 A | 11/1980 | Strope | |
| 4,246,893 A | 1/1981 | Berson | |
| 4,416,267 A | 11/1983 | Garren et al. | |
| 4,485,805 A | 12/1984 | Foster, Jr. | |
| 4,607,618 A | 8/1986 | Angelchik | |
| 4,694,827 A | 9/1987 | Weiner et al. | |
| 4,723,547 A | 2/1988 | Kullas et al. | |
| 4,739,758 A | 4/1988 | Lai et al. | |
| 4,857,029 A | 8/1989 | Dierick et al. | |
| 4,899,747 A | 2/1990 | Garren et al. | |
| 4,925,446 A | 5/1990 | Garay et al. | |
| 5,049,106 A | 9/1991 | Kim et al. | |
| 5,129,915 A | 7/1992 | Cantenys | |
| 5,234,454 A | 8/1993 | Bangs | |
| 5,259,399 A | 11/1993 | Brown | |
| 5,431,917 A | 7/1995 | Yamamoto et al. | |
| 5,852,889 A | 12/1998 | Rinaldi | |
| 5,868,141 A | 2/1999 | Ellias | |
| 6,427,089 B1 | 7/2002 | Knowlton | |
| 6,454,785 B2 | 9/2002 | De Hoyos Garza | |

FOREIGN PATENT DOCUMENTS

| | | | |
|---|---|---|---|
| EP | 0 246 999 | | 11/1987 |
| WO | WO 01/68007 A1 | | 9/2001 |
| WO | WO 02/16001 | * | 2/2002 |

OTHER PUBLICATIONS

VanSonnenberg et al., "Percutaneous Gastrostomy: Use of Intragastric Ballon Support," Radiology, Aug. 1984, vol. 152, No. 2, pp 531-532.

(Continued)

*Primary Examiner*—Michael Thaler
(74) *Attorney, Agent, or Firm*—Kenyon & Kenyon

(57) ABSTRACT

A self-inflating, intragastric balloon device is activated by addition of an activating liquid into an acid or water soluble vessel located within the balloon. After an approximately pre-determined time period post-activation, the activating liquid breaches the vessel wall and causes contact between an acid in liquid form and an emissive substance within the balloon, causing it to inflate. The device is conveniently provided to medical personnel as part of a kit that further contains a syringe and the activating liquid. The device also can have acid or pepsin degradable portions that cause it to deflate after residing in the stomach for a prolonged period of time during which it imparts a feeling of satiety in the patient.

22 Claims, 7 Drawing Sheets

OTHER PUBLICATIONS

Benjamin et al., "Double-Blind Controlled Trial of the Garren-Edwards Gastric Bubble: An Adjunctive Treatment for Exogenous Obesity", Gastroenterology, vol. 95, No. 3, Sep. 1988, pp 581-588.

Mathus-Vliegen et al., "Intragastric Balloon in the Treatment of Super-morbid Obesity - Double-Blind, Sham-Controlled, Crossover Evaluation of 500-Mililiter Balloon", Gastroenterology, vol. 3, No. 1, 1984, pp. 43-50.

F.E. Eckhauser et al. "Hydrostatic Balloon Dilatation for Stomal Stenosis after Gastric Partitioning" Surgical Gastroenterology, vol. 3, No. 1, 1984. pp. 43-50.

Nieben et al. "Intragastric Balloon as an Artificial Bezoar for Treatment of Obesity"The Lancet, vol. 1, 1982, pp. 198-199.

Geliebter et al. "Gastric balloon to treat obesity: a double-blind study in nondieting subjects", The American Journal of Clinical Nutrition, 1990, pp. 584-588.

* cited by examiner

SELF-INFLATING INTRAGASTRIC VOLUME-OCCUPYING DEVICE

FIELD OF THE INVENTION

The present invention relates to medical devices for curbing appetite and, more particularly, to intragastric balloons

BACKGROUND OF THE INVENTION

Obesity is a major health problem in developed countries. In the United States, the complications of obesity affect nearly one in five individuals at an annual cost of approximately $40 billion. Except for rare pathological conditions, weight gain is directly correlated to overeating.

Noninvasive methods for reducing weight include either increasing metabolic activity to burn calories or reducing caloric intake, either by modifying behavior or with pharmacological intervention to reduce the desire to eat. Other methods include surgery to reduce the stomach's volume, banding to limit the size of the stoma, and intragastric devices that reduce the desire to eat by occupying space in the stomach.

Intragastric volume-occupying devices provide the patient a feeling of satiety after having eaten only small amounts of food. Thus, the caloric intake is diminished while the subject is satisfied with a feeling of fullness. Currently available volume-occupying devices have many shortcomings. For example, complex gastrotomy procedures are required to insert some devices.

Clinical use of intragastric balloons has been ongoing for several years, and its success in the treatment of certain individuals with morbid obesity is well accepted. Volume-occupying devices for use in obesity reduction were developed in the late 1970's and early 1980's. These early designs had multiple complications that caused them not to gain widespread acceptance at the time. Newer designs were developed in the late 1980's, and have led to their wider acceptance in European clinics.

U.S. Pat. No. 4,133,315 discloses an apparatus for reducing obesity comprising an inflatable, elastomeric bag and tube combination. According to the '315 patent, the bag can be inserted into the patient's stomach by swallowing. The end of the attached tube distal to the bag remains in the patient's mouth. A second tube is snaked through the nasal cavity and into the patient's mouth. The tube ends located in the patient's mouth are connected to form a continuous tube for fluid communication through the patient's nose to the bag. Alternatively, the bag can be implanted by a gastronomy procedure. The bag is inflated through the tube to a desired degree before the patient eats so that the desire for food is reduced. After the patient has eaten, the bag is deflated. As taught by the '315 patent, the tube extends out of the patient's nose or abdominal cavity throughout the course of treatment.

U.S. Pat. Nos. 5,259,399, 5,234,454 and 6,454,785 disclose intragastric volume-occupying devices for weight control that must be implanted surgically.

U.S. Pat. Nos. 4,416,267; 4,485,805; 4,607,618; 4,694,827, 4,723,547; 4,739,758; 4,899,747 and European Patent No. 246,999 relate to intragastric, volume-occupying devices for weight control that can be inserted endoscopically. Of these, U.S. Pat. Nos. 4,416,267; 4,694,827; 4,739,758 and 4,899,747 relate to balloons whose surface is contoured in a certain way to achieve a desired end. In the '267 and '747 patents, the balloon is torus-shaped with a flared central opening to facilitate passage of solids and liquids through the stomach cavity. The balloon of the '827 patent has a plurality of smooth-surfaced convex protrusions. The protrusions reduce the amount of surface area which contacts the stomach wall, thereby reducing the deleterious effects resulting from excessive contact with the gastric mucosa. The protrusions also define channels between the balloon and stomach wall through which solids and liquids may pass. The balloon of the '758 patent has blisters on its periphery that prevent it from seating tightly against the cardia or pylorus.

The balloons of the '747 and '827 patents are inserted by pushing the deflated balloon and releasably attached tubing down a gastric tube. The '547 patent discloses a specially adapted insertion catheter for positioning its balloon. In the '758 patent, the filler tube effects insertion of the balloon. In U.S. Pat. No. 4,485,805, the balloon is inserted into a finger cot that is attached by string to the end of a conventional gastric tube that is inserted down the patient's throat. The balloon of the EP '999 patent is inserted using a gastroscope with integral forceps.

In the '267, '827, '758, '747, '805 and EP '999 patents, the balloon is inflated with a fluid from a tube extending down from the patient's mouth. In these patents, the balloon also is provided with a self-sealing hole ('827), injection site ('267, '747), self-sealing fill valve ('805), self-closing valve (EP '999) or duck-billed valve ('758). The '547 patent uses an elongated thick plug and the balloon is filled by inserting a needle attached to an air source through the plug.

U.S. Pat. No. 4,607,618 describes a collapsible appliance formed of semi-rigid skeleton members joined to form a collapsible hollow structure. The appliance is not inflatable. It is endoscopically inserted into the stomach using an especially adapted bougie having an ejector rod to release the collapsed appliance. Once released, the appliance returns to its greater relaxed size and shape.

None of the foregoing patents discloses a free-floating, intragastric, volume-occupying device that can be inserted into the stomach simply by the patient swallowing it and letting peristalsis deliver it into the stomach in the same manner that food is delivered.

U.S. Pat. No. 5,129,915 relates to an intragastric balloon that is intended to be swallowed and that inflates automatically under the effect of temperature. The '915 patent discusses three ways that an intragastric balloon might be inflated by a change in temperature. A composition comprising a solid acid and non-toxic carbonate or bicarbonate is separated from water by a coating of chocolate, cocoa paste or cocoa butter that melts at body temperature. Alternatively, citric acid and an alkaline bicarbonate coated with non-toxic vegetable or animal fat melting at body temperature and which placed in the presence of water, would produce the same result. Lastly, the solid acid and non-toxic carbonate or bicarbonate are isolated from water by an isolation pouch of low-strength synthetic material which it will suffice to break immediately before swallowing the bladder. Breaking the isolation pouches causes the acid, carbonate or bicarbonate and water to mix and the balloon to begin to expand immediately. A drawback of thermal triggering of inflation as suggested by the '915 patent is that it does not afford the degree of control and reproducibility of the timing of inflation that is desirable and necessary in a safe self-inflating intragastric balloon.

After swallowing, food and oral medicaments reach a patient's stomach in under a minute. Food is retained in the stomach on average from one to three hours. However, the residence time is highly variable and dependent upon such factors as the fasting or fed state of the patient. Inflation of a self-inflating intragastric balloon must be timed to avoid premature inflation in the esophagus that could lead to an esophageal obstruction or belated inflation that could lead to intestinal obstruction.

There remains a need for a free-floating intragastric balloon device that can be delivered to the stomach by conventional oral administration and that controllably inflates after an approximately predetermined delay time period.

SUMMARY OF THE INVENTION

Figure 1A:
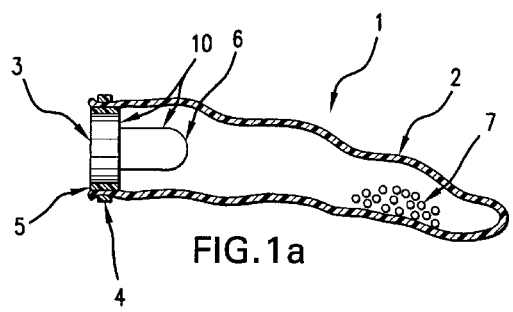
FIG. 1 depicts cross-sectional views of a self-inflating intragastric devices in accordance with the invention: (a) a device having an emissive substance containing within the lumen of the balloon, (b) a device having an emissive substance and a solid acid contained within the lumen of the balloon, (c) a device having an emissive substance contained in the lumen and a solid acid contained in a separate vessel, and (d) a device having an emissive substance contained in the vessel and a solid acid contained in the lumen of the balloon.

In a first aspect, the present invention provides a self-inflating intra-gastric device that is useful for curbing appetite and engorging the stomach attendant to a medical procedure. The device includes a substantially liquid-impermeable balloon that contains an emissive substance that gives off a gas when contacted with an acidic liquid and contains a vessel enclosing a space isolated from the emissive substance. Fluid communication from outside the balloon to the vessel is enabled by a self-sealing valve.

The device self-inflates at an approximately pre-determined time after activation. The device is activated by communicating an activating liquid from outside of the balloon into the vessel. The vessel is made, at least in part, of a soluble barrier material, that is breached by the activating liquid after an approximately predetermined delay time period. The device is administered to the subject during this time period. Breach of the vessel causes mixing of acid and the emissive substance resulting in emission of gas and inflation of the balloon.

Preferably, the device is sized and shaped so that it can be swallowed by the subject to whom it is administered. Alternatively, the device can be administered using endoscopic equipment known to those in the medical arts.

The device can be supplied as part of a kit to medical personnel who will administer the device in a non-toxic container that is sized to pass down the esophagus of the subject to whom it will be administered. The kit may further contain a pre-filled syringe or other container of activating liquid.

The invention further relates to the treatment of obesity and the performance of medical procedures on the abdomen using one or more of the medical devices of the invention.

In another aspect, the invention provides a self-inflating and self-deflating intragastric medical device. Medical devices conforming to this aspect of the invention include at least one portion of the device fabricated of an acid or pepsin degradable material. Such portions include the bladder portion of the balloon, the self-sealing valve, and a clamp that may be provided to hold the self-sealing valve in fluid-tight engagement with the bladder.

DETAILED DESCRIPTION OF THE PREFERRED EMBODIMENTS

In a first aspect, the present invention provides a self-inflating intragastric medical device useful for curbing appetite for the purpose of promoting weight loss. The device also is useful for engorging the stomach attendant to a medical procedure. For instance, it is known that intragastric balloons can be useful in the performance of a percutaneous gastrostomy. VanSonnenberg, Eric et al. *Radiology* 1984, 152, 531. The medical device includes a volume-occupying balloon and means to inflate the balloon once an approximately pre-determined time period has passed after activation.

Operation of the self-inflating intragastric medical device is best understood by consideration of its functional components. The device includes a balloon whose size is determined by the pressure of a fluid, in this case a gas, inside the lumen of the balloon. When inflated, gas pressure inside the balloon causes it to occupy a volume substantially greater than the volume it occupies when the gas pressure inside the balloon is the same or less than the ambient pressure outside the balloon. The balloon of this medical device occupies a substantial volume when inflated, preferably from about 200 $cm^3$ to about 800 $cm^3$ so as to significantly contribute to the attainment of a feeling of satiety when the device is used to curb appetite or to significantly engorge the stomach when it is used attendant to a medical procedure. However, for either of these purposes it is within the contemplation of the invention to insert one, two, several or more balloons in the stomach of the subject to whom the device is administered. While the uses with which the invention are most immediately concerned relate to human beings and medical treatment that is appropriate for them, the invention has veterinary applications as well, particularly for mammals. A balloon of a different size may be appropriate for a veterinary application.

The self-inflating intragastric medical device is sized to pass through the esophagus. The balloon must be in an uninflated condition to allow passage through the esophagus. In the uninflated condition, the size of the balloon's lumen is minimized. Thus, prior to administration, and preferably during manufacture, the balloon is sealed at ambient or reduced pressure relative to the pressure outside of the balloon. The device may be positioned in the stomach of a patient by inserting it down the throat while the patient is under sedation using well known medical instruments. Preferably, however, the device is swallowed by the patient and transported to the stomach by peristalsis.

The balloon self-inflates in the subject's stomach without an external source like a syringe or pump delivering fluid to it as it is inflating. Accordingly, it does not require attached feedlines running out of the subject's mouth or through the stomach wall to provide inflation fluid from an outside source.

In the present invention, self-inflation is achieved by the reaction of an acid with an emissive substance in the lumen of the balloon resulting in the generation of gas. Inflation occurs because of the substantial fluid-impermeability of the balloon and the greater volume occupied by molecules of a gas than the same number of solid molecules at the same temperature and pressure.

Acids useful in the device include acetic acid, citric acid and solutions thereof and solutions of hydrochloric acid. A preferred solvent for preparing solutions is water although the acid may be sufficiently soluble in another solvent, like ethanol, that substitution of another solvent is acceptable, provided the alternative solvent does not cause the subject to experience adverse side effects.

The emissive substance liberates gas when contacted with a solution of citric acid, acetic acid or solution thereof, or a solution of hydrochloric acid (although other acids may be used, an emissive substance that liberates gas upon contact with them will also, as a general matter, liberate gas when contacted with the preferred acids of the invention). Preferred emissive substances are alkaline metal carbonates and bicarbonates and solutions, preferably aqueous solutions, thereof Especially preferred emissive substances are sodium bicarbonate ($NaHCO_3$) and potassium bicarbonate ($KHCO_3$) which liberate carbon dioxide when they react with acid.

In addition to the emissive substance, the balloon encloses a vessel that defines a space separate and isolated from the rest of the lumen of the balloon. The vessel is formed, at least in part, of a soluble barrier material. Soluble barrier materials are thermally resilient rigid materials that melt above 30° C. more preferably above 50° C. Soluble barrier materials dissolve in water, organic acids that are liquid at room temperature or solutions of mineral or organic acids. Soluble barrier materials meeting these criteria include, but are not necessarily limited to gelatin, xanthan gum and cellulose derivatives and compositions described in U.S. Pat. No. 5,431,9917 and Japanese Patent Laid-Open Nos. 61-100519 and 62-26606, and the like, with gelatin being the most preferred soluble barrier material.

To prevent premature inflation of the balloon, the acid and emissive substance (or substances) are isolated from each other until the balloon is inserted into the subject's stomach. There are several ways by which the acid and emissive substance can be isolated from each other in accordance with this invention. A solid acid and solid emissive substance can be in physical proximity or even contact in the lumen of the balloon and yet be isolated chemically because they are both in a solid state in which they are unable to react and generate gas. Alternatively, they can be isolated physically by positioning one in the vessel and the other in the lumen of the balloon. Accordingly, as used in this disclosure the term "isolated" means physical separation by a barrier and chemical separation due to the solid physical state of the acid and emissive substance.

In one embodiment, the self-inflating intragastric device includes an uninflated balloon containing an emissive substance and an empty vessel in its lumen. In alternative embodiments, the balloon also contains a solid acid, in which case the device may conform to any one of the following embodiments: (1) the solid acid is located within the vessel and the emissive substance is located in the lumen of the balloon, (2) the solid acid and the emissive substance are both located in the lumen and the vessel is empty and (3) the solid acid is located in the lumen and the emissive substance is located in the vessel. A preferred solid acid for these embodiments is citric acid.

The self-inflating intragastric device of the present invention may be supplied to appropriately trained medical personnel as part of a kit. A container such as a vial, ampule or pre-filled syringe containing an activating liquid is also supplied as part of the kit. The nature of the activating liquid depends upon whether the balloon is provided with a solid acid. In an embodiment wherein the balloon does not contain a solid acid, the activating liquid is either an organic acid that is liquid at room temperature or a solution of a mineral or organic acid. In an embodiment wherein the balloon does contain a solid acid, the activating liquid can be essentially any aqueous solution whose solutes do not interfere with inflation of the balloon, the preferred activating liquid in such embodiments being substantially pure water. Textual materials containing instructions on how to activate, administer, use and/or cease using the device also may be supplied as part of the kit.

The acid and emissive substance are caused to react after an approximately predetermined delay time period by activating the device prior to administration to the patient, preferably within a minute prior to administration. To activate the device, the activating liquid is communicated into the vessel. Communication of the activating liquid into the vessel commences dissolution of the vessel, or soluble portion thereof, leading to a breach of the vessel wall. After breach occurs, the acid and the emissive substance cease to be isolated; they react liberating gas and causing the balloon to inflate. This should occur only after the device is in the patient's stomach. Thus, the activating liquid and soluble material from which the vessel is formed are selected with a view to controlling the time period between activation of the device and the moment when inflation begins. If that time period is too short, the balloon may obstruct the esophagus. If that time period is too long, the balloon may pass from the stomach into the intestine before inflating and cause an intestinal obstruction. For minimum risk of these possibilities, a delay time period of from about 1 min. to about 10 min. is optimal, although it may vary depending upon the patient. Although other combinations of activating liquid and soluble material may be arrived at by routine experimentation, the following combinations have been found suitable in practice.

In a previously described embodiment of the self-inflating intragastric device, the balloon contains the emissive substance in the lumen and an empty vessel, without a solid acid. For this embodiment, a preferred soluble barrier material from which to fabricate at least a portion of the vessel is gelatin. Preferred activating liquids for this embodiment are mixtures of from about 25% to about 50% (v/v) acetic acid and from about 50% to about 75% (v/v) water, more preferably about 33% acetic acid and 67% (v/v) water.

In a second embodiment of the self-inflating intragastric device, the balloon contains the emissive substance in the lumen of the balloon and a solid acid, like citric acid, in the vessel. In this embodiment, the preferred activating liquid is water. Upon communication into the vessel, the water dissolves the solid acid and dissolves the vessel, such that upon breach of the vessel wall a solution of the acid contacts the emissive substance, whereupon they can react to liberate gas and inflate the balloon.

In yet another embodiment of the self-inflating medical device of this invention, the balloon contains both the solid acid and the emissive substance in the lumen and the vessel is empty. In this embodiment, the preferred activating liquid is water. Upon communication into the vessel, the water dissolves at least a portion of the vessel and upon breach of the vessel enters the lumen of the balloon, where it dissolves the solid acid and emissive substance causing them to cease being chemically isolated and able to react to produce gas.

To activate the balloon, the activating liquid is communicated from outside of the balloon (which must be substantially liquid impenetrable afterwards) to the vessel, preferably by means of a self-sealing valve. In this disclosure, the term "self-sealing valve" is used broadly to include any portal that can be opened to allow fluid communication from one side of the portal to the other side and that closes or seals itself without cumbersome mechanical manipulations. The sorts of articles encompassed by the term include a septum and a duck billed valve, such as those of U.S. Pat. No. 4,739,758. A septum is an elastomer body or segment that yields to a hollow needle and that deforms to close the hole left by the needle after it is withdrawn. Known mechanical valves of the type that have rotating or sliding cores mated to a valve seat are not preferred for this application because they are typically too large for convenient oral administration and, if sized for easy administration, would be cumbersome to operate, delicate and/or likely to cause discomfort while in the patient's body. Of course, such valves are appropriately used on equipment used in conjunction with the device such as a syringe if so desired so long as they are not non-releasably connected to the device. Preferably, the self-sealing valve is a septum. As described more fully below, the septum may be discrete part of the balloon attached to a bladder component of the balloon with a substantially liquid-impermeable seal or it may be a segment of a balloon formed of self-sealing material that is identified, e.g. by markings on the exterior surface of the balloon.

The vessel may be connected to the self-sealing valve by a conduit through which the activating liquid passes to reach the vessel. Alternatively and yet more preferably, the self-sealing valve is a septum and the side of the septum facing the interior of the balloon forms a wall of the vessel. In such a construction, the vessel is formed of and defined by attachment of a receptacle fabricated of soluble barrier material having a mouth to the interior side of the septum. Thus, the combination of the septum and the receptacle define the size and shape of the vessel and the space that it encloses. The activating liquid is communicated directly to the vessel by inserting the tip of the needle of a syringe containing the activating liquid through the septum and advancing the plunger. The plunger may then be withdrawn and advanced again one or more times to allow air to escape from the vessel. Alternatively, the vessel may be vented by inserting the tip of a second hollow needle (which need not be attached to a syringe) through the septum through which air can escape. Yet another alternative is to evacuate the vessel, which may be accomplished coincident with evacuating the balloon, if so desired, during fabrication.

After the device has been activated, the device is administered to the patient. Although the length of the approximately pre-determined delay time until inflation will affect the speed with which the activated device should be administered, administration should occur promptly after activation, preferably within about a minute thereafter. Although the device can be administered using well known techniques of gastric endoscopy known in the art, the device preferably is administered orally as one would administer a capsule or tablet, by the patient swallowing the device. To facilitate swallowing, the device may further comprise a container. The container should be made of a material that dissolves in gastric fluid more rapidly than the vessel, or soluble portion thereof, dissolves in the activating fluid. To insert the balloon into the container, the uninflated or evacuated balloon is compacted, such as by rolling, folding or wadding into a mass small enough to be inserted into the container.

While compacting, care should be taken that the self-sealing valve is exposed on the surface of the compacted balloon. The container is preferably transparent, semitransparent or is marked to facilitate identification of the self-sealing valve after the balloon has been compacted. When the location of the self-sealing valve is visible from outside the container, the device can be activated while in the container by simply piercing the container with the needle used to inject the acid. This does not affect the delay until inflation as that is controlled by the degradation rate of the inner vessel. Hard gelatin capsules are apt containers to ease swallowing of the device by the patient. Swallowing can, of course, be further eased and the device may reach the stomach more rapidly if the patient swallows the device with a gulp of water.

The volume that the balloon must occupy when inflated affects the quantity of the emissive substance and optional solid acid that is required as well as the amount of film or fabric material that is used to make balloon. These factors affect the balloon's size after it is compacted. The largest standard sized hard gelatin capsule designed for oral administration to humans is the 000 size capsule. Large balloons of this invention which can inflate to 600–800 ml will not necessarily compact to that size. Containers for 600–800 ml balloons preferably measure from about 2 cm to about 6 cm by about 0.5 cm to about 2 cm by about 0.5 cm to about 2 cm. More preferably the container for such balloons are about 4×1×1 cm. Two piece hard gelatin capsules with these dimensions can be readily produced using techniques described below for making a receptacle and which also are well known in the art. In addition, a veterinary capsule is a viable alternative. Although not intended for routine drug administration to humans due to their large size, many of the smaller veterinary sizes can be swallowed by full grown adults without undue risk. Preferred veterinary size capsules for the container are standard sizes 13, 12, 11, 12el and 10, which are available for instance from Torpac, Inc. (Fairfield, N.J.), with size 12el measuring 6×1.3 cm being especially preferred. The veterinary capsules may be used as received from a supplier. Alternatively, they may be modified by cutting, reshaping and resealing to obtain a container of the desired volume. For instance, an about 4×1×1 cm container can be made by cutting off the open ends of size 12el half-capsules at a point that allows the remaining portions of the half-capsules to be pressed together to a length of no greater than about 4 cm. Further, a longitudinal segment may be removed from the half-capsules, and the edges resealed to reduce the cross-sectional dimensions of the capsule. When a plurality of self-inflating balloons of smaller volume are used, the device may be sized to fit into a 000 or even smaller capsule designed for routine oral administration of drugs to humans.

Having thus described the medical device of the present invention with reference to its functional components, it will now be further illustrated with a description of exemplary embodiments depicted in the figures.

Turning now to FIG. 1 and in particular to FIG. 1(a) there is depicted a self-inflating, intragastric device 1 in accordance with the present invention. As illustrated, device 1, includes bladder 2. Bladder 2 can assume any shape upon inflation, e.g. spherical, oblong, drum or elongated. In addition, the balloon can have a contoured surface to facilitate transport of food from the cardia to the pylorus or to minimize contact between the balloon and the stomach wall as taught in U.S. Pat. Nos. 4,416,267; 4,694,827; 4,739,758 and 4,899,747 or it can have other surface contours. Preferably, bladder 2 assumes a generally spherical shape upon inflation.

Bladder 2 can be made of any substantially liquid-impermeable material. The material may be non-elastic or semi-elastic, such as Dacron®, Nylon® and the like, with Nylon® being preferred. Alternatively, the material may be highly elastic, such as rubber, latex and the like. Further, the bladder may have a mono-layer, bi-layer or multi-layer construction. For instance, a bladder may have an inner layer of Nylon® or ethyl vinyl acetate and an outer layer of silicone for better biocompatibility. In addition, the substantially liquid-impermeable material could contain a radiopaque substance to enable visualization of the balloon in the patient's stomach. Alternatively, the balloon could have band of radiopaque material like a metal foil around its circumference to enable visualization.

In the device of FIG. 1(a), the uninflated balloon is elongate and has one open end. A septum 3 is positioned in the opening of bladder 2 and is in fluid-tight engagement with the interior surface of the bladder. The septum and bladder may be adhered by any adhesive that forms a fluid-tight seal between the septum and bladder. They also may be engaged by clamping means 4 that encircles the open end of the balloon around the septum. As illustrated in FIG. 1(a), a rigid sleeve 5 may encircle septum 3 and mediate the fluid-tight seal between septum 3 and bladder 2.

The exemplary device of FIG. 1(a) further has a receptacle 6 formed of soluble barrier material. As illustrated, receptacle 6 is generally cylindrically shaped and has an open end, or mouth, and a closed end, like half of a gelatin capsule. An especially preferred receptacle is made of gelatin and has an inner volume of from about 1 cm$^3$ to about 3 cm$^3$, more preferably from about 1 cm$^3$ to about 2 cm$^3$, and most preferably about 1.7 cm$^3$. A gelatin receptacle can be made using well known techniques in the art. A solution of gelatin in water is prepared. A stainless steel pin is dipped into the solution and then withdrawn. A film of gelatin that adheres to the end of the pin is dried with heat and/or circulating air. Once dried, the hardened gelatin can be slid off the end of the pin and, if necessary, its edges can be trimmed to produce a smooth mouth surface. The thickness of the receptacle wall can be adjusted by varying the viscosity of the gelatin solution and thereby control the length of time between activation and inflation. A receptacle of nearly any desired size also can be made from commercially available gelatin capsules. Commercial capsules consist of two half-capsules. If neither of the half-capsules of a standard size has the desired volume, then the half-capsule that fits over the other can be used to increase the volume of the smaller half-capsule. The closed end is cut off of the larger half-capsule. The tubular segment from the larger half capsule is slid over the smaller half capsule and positioned so that the modified half-capsule has the desired inner volume. A viscous gelatin solution can be painted along the edge of the tubular segment that encircles the smaller half-capsule to make it fluid-tight after it dries.

The mouth of receptacle 6 should be smooth so that it will bond to the surface of the septum facing the interior with a fluid-tight seal. The seal can be effected with any non-toxic adhesive that will produce a fluid-tight seal. The seal also can be effected by moistening the mouth of the receptacle causing the soluble barrier material to soften and then pressing the mouth against the septum until it has dried and rehardened.

In the illustrative embodiment of FIG. 1(a), an emissive substance 7 is contained within the lumen of bladder 2. To activate the device depicted in FIG. 1(a), a liquid organic acid or solution of mineral or organic acid is injected through the septum 3 into vessel 10. In this disclosure, like numbers indicate like parts in the drawings.

Figure 1C:
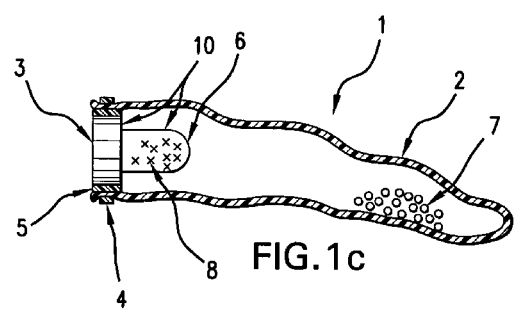
Figure 1B:
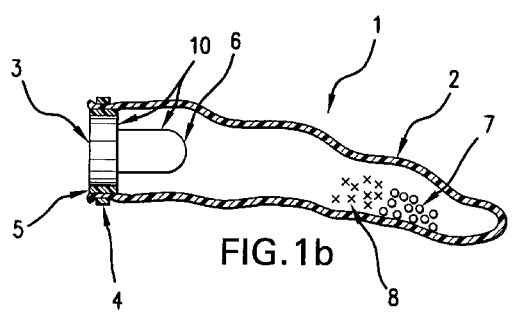

In another illustrative embodiment depicted in FIG. 1(b), the lumen of bladder 2 contains in addition to the emissive substance 7 (indicated by "o"s), a solid acid 8 (indicated by "x"s). To activate the device depicted in FIG. 1(b), an aqueous solution, preferably substantially pure water is injected through septum 3 into vessel 10.

In another illustrative embodiment depicted in FIG. 1(c), the emissive substance 7 is contained in the lumen of bladder 2 and a solid acid 8 is contained in the vessel. To activate the device depicted in FIG. 1(c), an aqueous solution, preferably substantially pure water is injected through septum 3 into vessel 10.

Figure 1D:
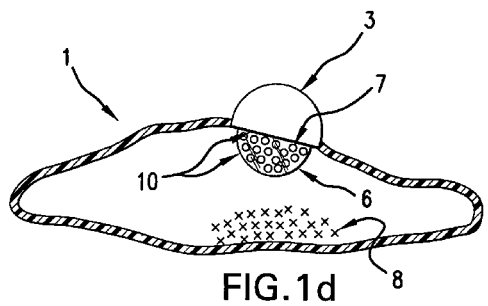
Figure 2A:
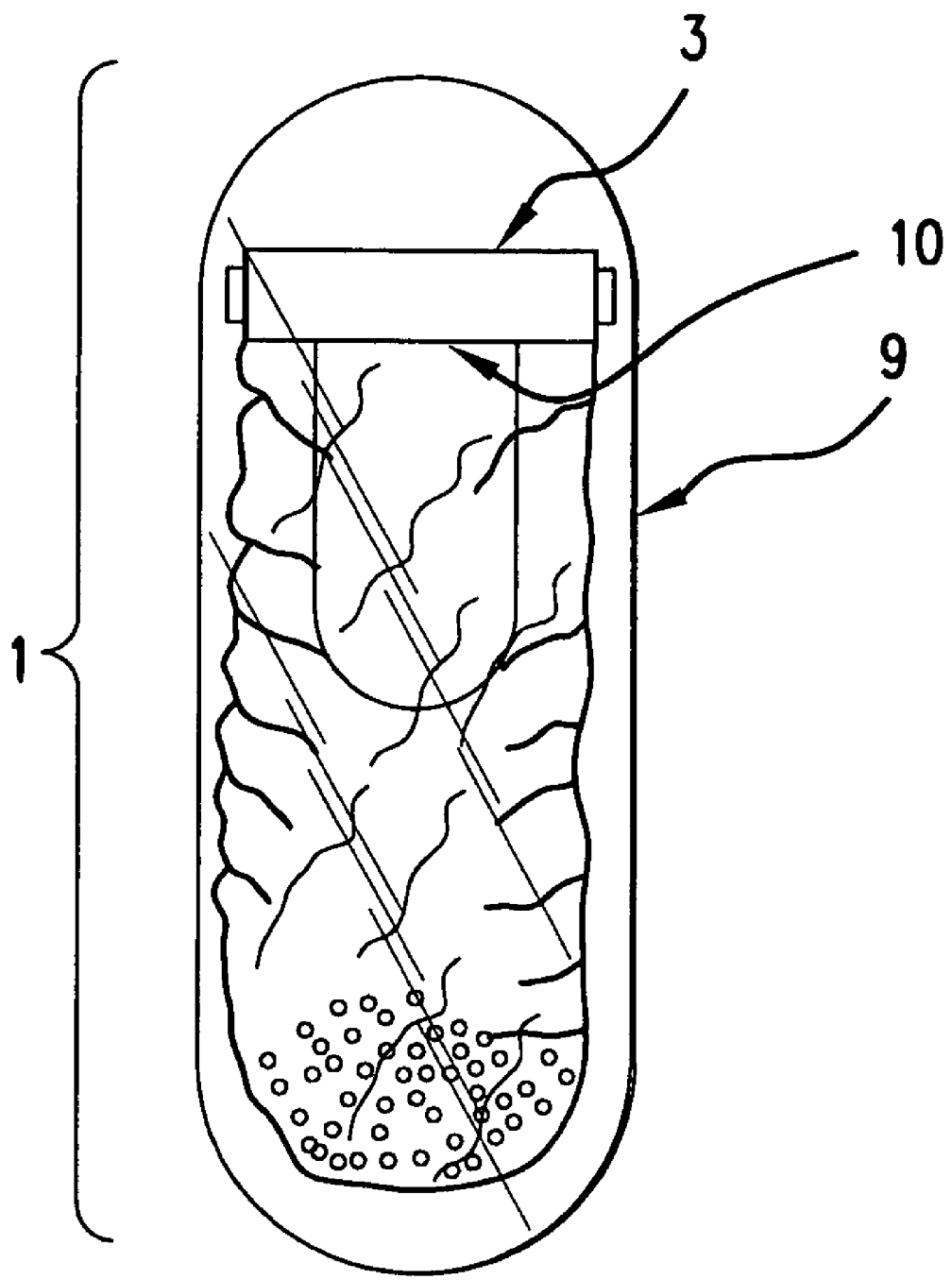
FIG. 2: (a) depicts a device in accordance with the invention enclosed in a container as it might by received by the nurse or doctor who will administer it, (b) depicts activation of the device by communication of an acid through a self-sealing valve into an acid degradable vessel, (c) depicts the device shortly after being swallowed by the patient, (d) depicts the device after reaching the stomach, the vessel having been breached, the balloon beginning to inflate and the container beginning to degrade, (e) the device partially inflated, and (D) the device fully inflated.
Figure 2B:
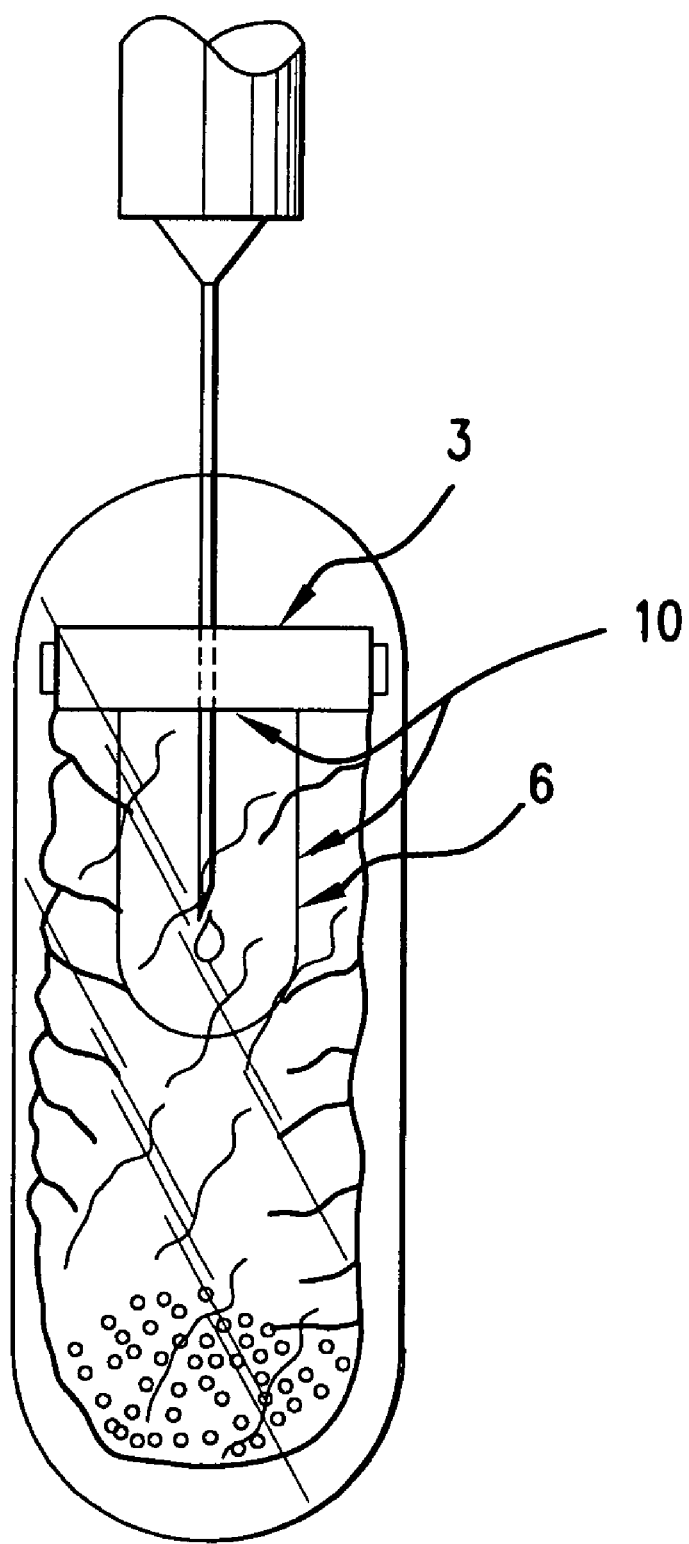
Figure 2C:
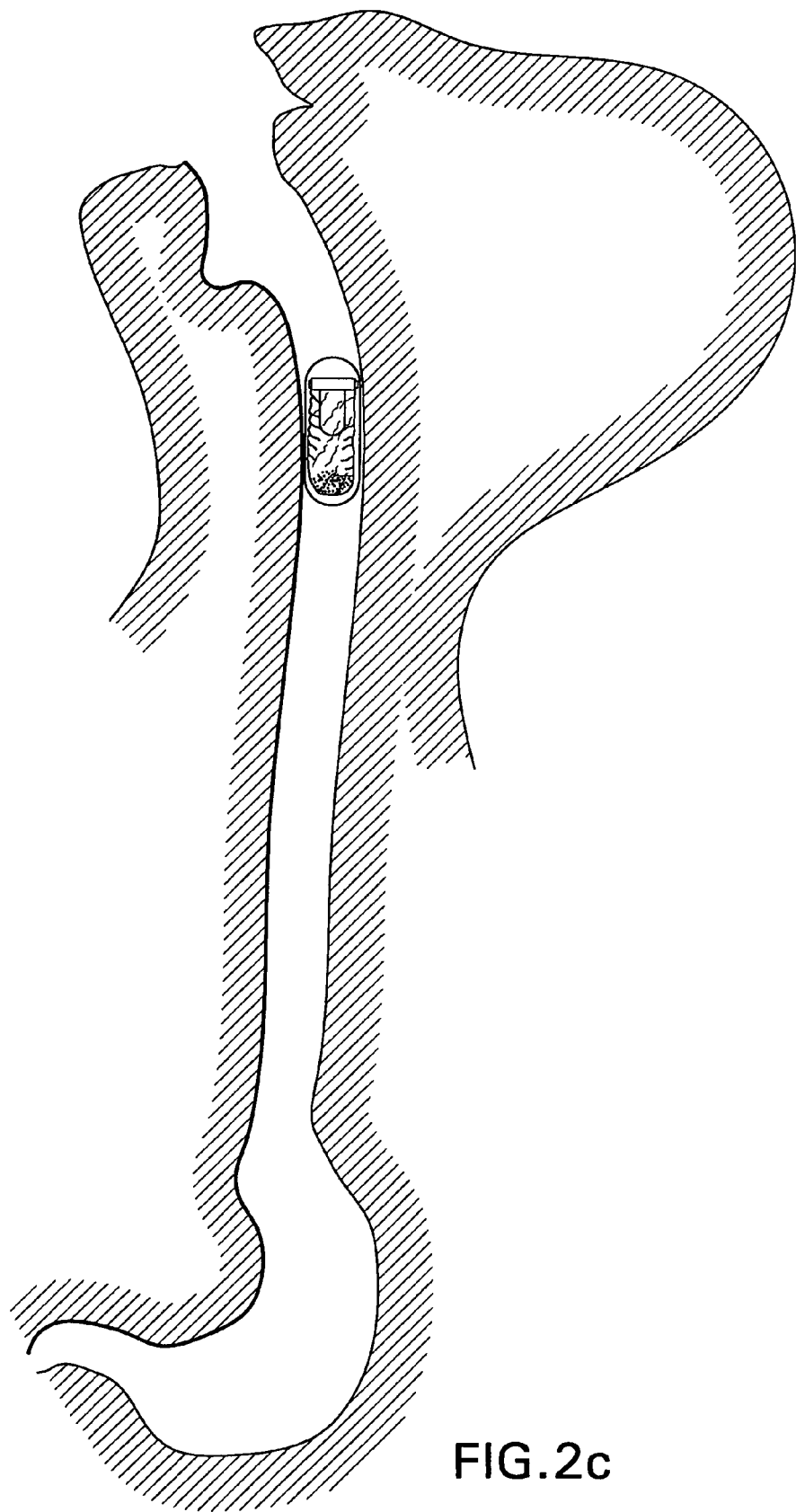
Figure 2D:
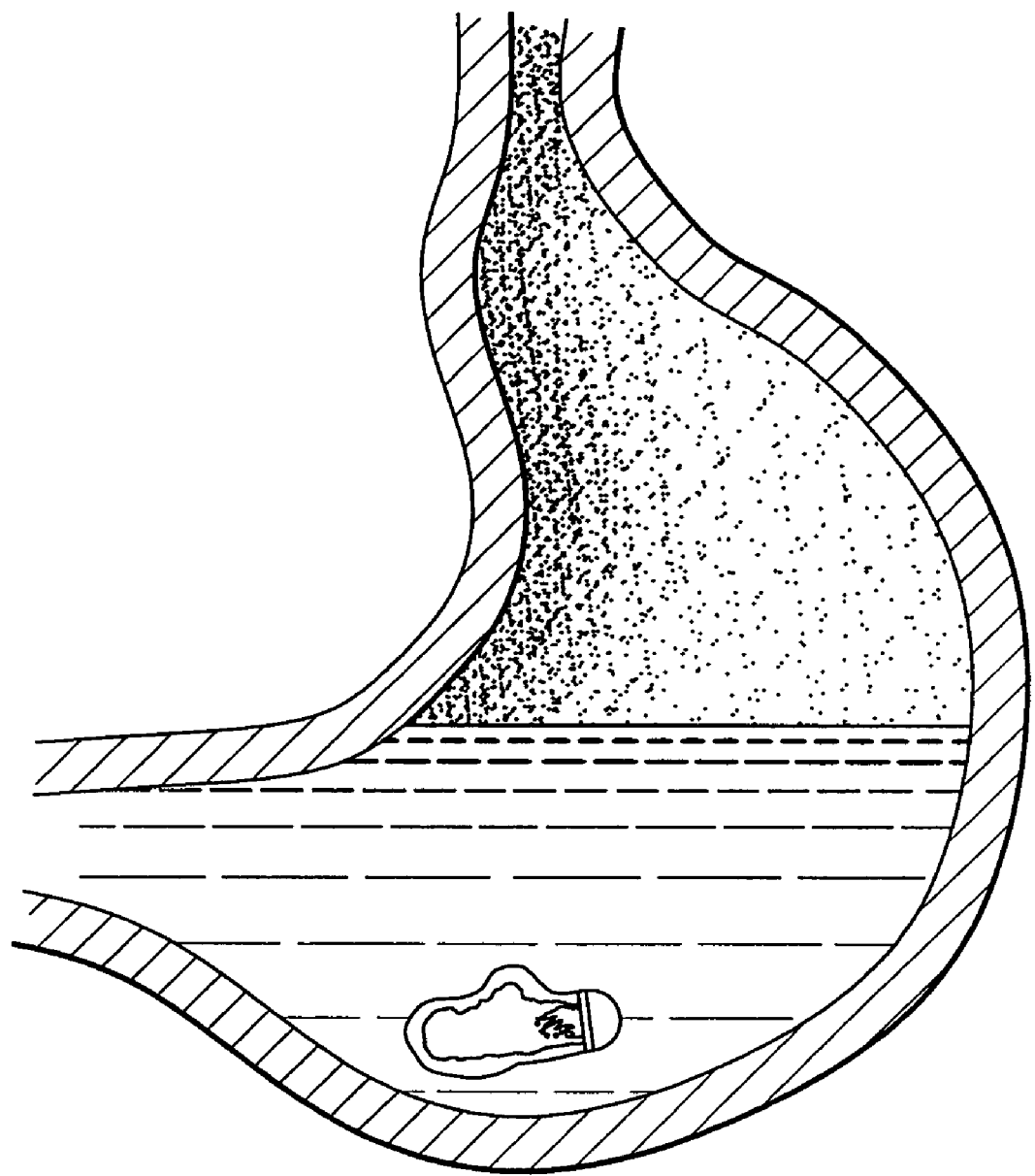
Figure 2E:
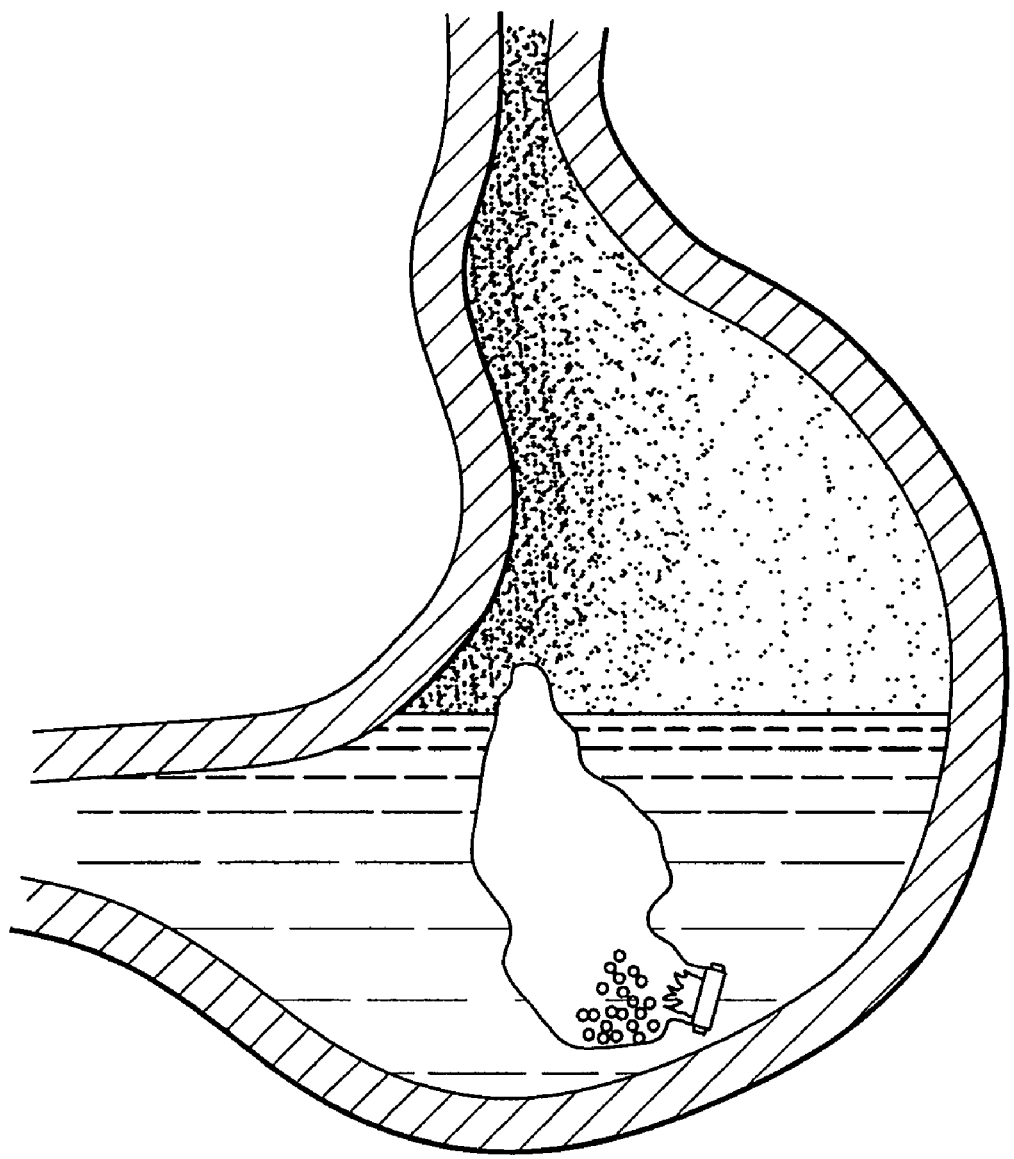
Figure 2F:
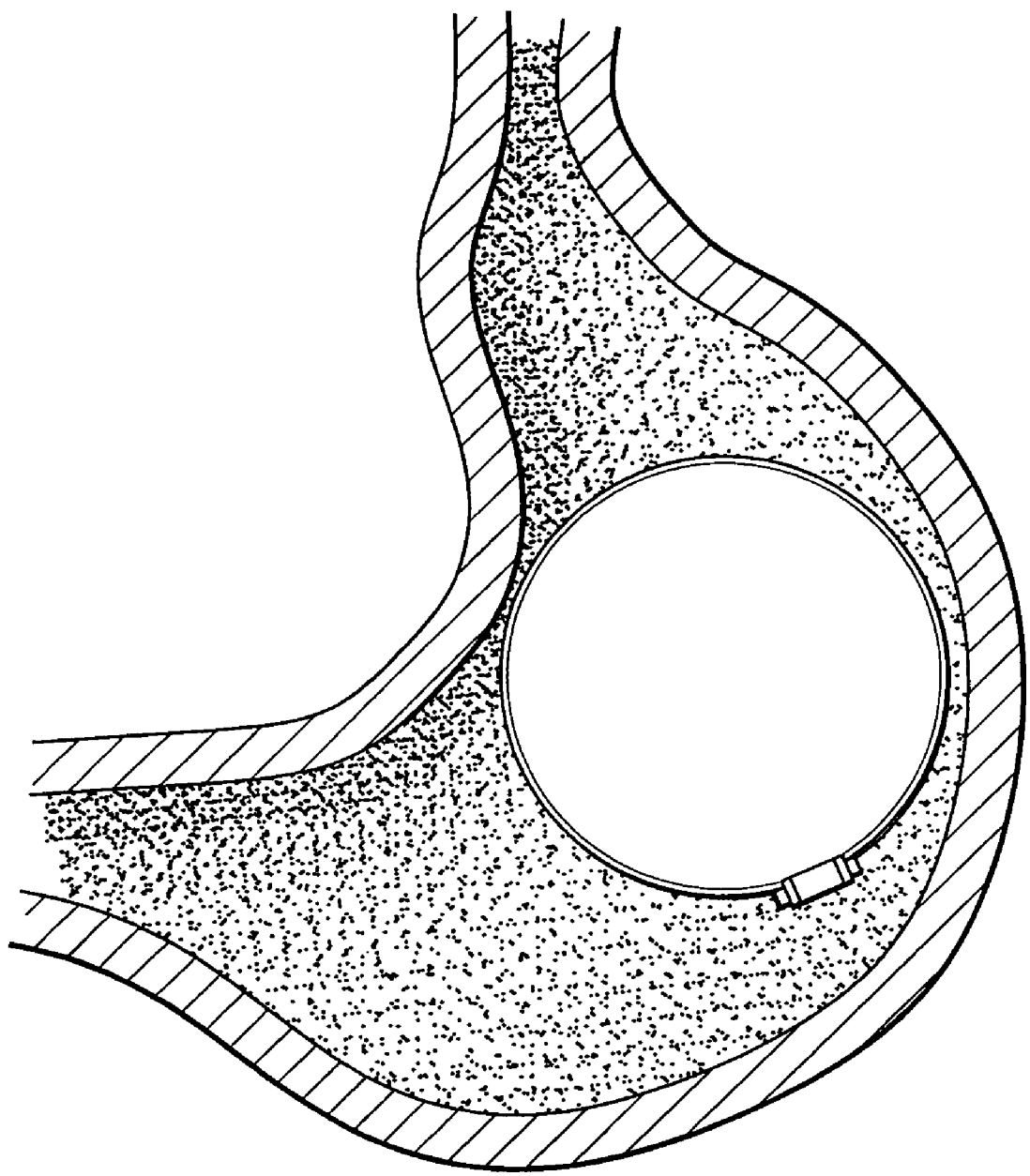

In another illustrative embodiment depicted in FIG. 1(d), the emissive substance 7 is contained within the vessel and a solid acid 8 is contained in the lumen. To activate the device depicted in FIG. 1(d), a non-acidic aqueous solution, preferably substantially pure water is injected through septum 3 into vessel 10. FIG. 1(d) also illustrates another construction. In the device of FIG. 1(d) the balloon is made of a self sealing material. Septum 3 is integral to the balloon and constitutes a thickened portion of the balloon wall formed during molding. Of course, the choice of location of the emissive substance 7 and optional solid acid 8 can be made independently of the construction details of the device.

FIG. 2 illustrates use of the device. In FIG. 2(a), the device of FIG. 1(a) has been compacted and encapsulated in container 9, in this case a 12el hard gelatin capsule that has been shortened as previously described. FIG. 2(b) shows injection of acid into the vessel 10 defined by receptacle 6 and interior-face of septum 3. Immediately after swallowing, the device 1 travels down the esophagus (FIG. 2(c)) and reaches the stomach. In the stomach, the container degrades under the action of gastric fluid and, thereafter, the vessel wall is breached allowing contact between the acid and emissive substance (FIG. 2(d)). Emission of gas inflates the balloon (FIG. 2(e)) until the emissive substance and/or acid is consumed, at which point the balloon should be inflated to a volume (FIG. 2(f)) approximately predetermined and controlled by the quantity of emissive substance present in the balloon. The quantity of emissive substance can be determined by routine experimentation or from knowledge of the stoichiometry of the gas generating reaction, the formula weight of the emissive substance, the desired pressure within the balloon and the ideal gas law. When the emissive substance is sodium bicarbonate or potassium bicarbonate and the balloon is sized to occupy from about 200 cm$^3$ to about 800 cm$^3$, then amount of emissive substance used will typically be in the range of from about 1 g to about 8 g.

The benefit of convenience to the patient and medical personnel is provided by the invention whether the balloon deflates automatically or is deflated manually and withdrawn by a medical procedure.

Another aspect of the present invention is the providing of an intragastric, volume-occupying device that self-deflates after an approximately pre-determined, prolonged period of time. During ordinary use, the device will reside in the subject's stomach for the entire period between inflation and deflation Preferably, the balloon remains inflated for from about 20 days to about 60 days.

After deflation, the device can pass through the pylorus and the rest of the digestive system without injury.

Self-deflation is achieved in the self-deflating device of the present invention by using slowly biodegradable, acid degradable or pepsin degradable materials (hereafter "degradable materials") in its construction. Accordingly, sleeve 5 can be made using a material that degrades in the stomach. Alternatively, the clamping means can be made of degradable materials. Prefered biodegradable materials from which to make a degrading sleeve or clamp are polyglycolide (Dexon®), poly(1-lactide), poly(d, 1-lactide), poly(lactide-co-glycolide), poly(ξ-caprolactone), poly(dioxanone), poly(glycolide-co-trimethylene carbonate), poly(hydroxybutyrate-co-hydroxyvalerate), polyglyconate (Maxon®) polyanhydrides or polyorthesters, Yet more preferred biodegradable materials are polydioxanone, Monocryl® (poliglecaprone) and Vicryl®. One especially preferred degradable material is biodegradable suture material, more particularly suture material made from polyglyconate (Maxon®), polyglycolide (Dexon®), poly(ξ-caprolactone) which is commercially available from Ethicon, Inc. (Somerville, N.J.) under the tradename Monacryl® and poly(dioxanone), also available from Ethicon. Combinations of polymeric material also may be used. These could be used where the properties of combined polymers contribute to better functioning of the device. For example, a more resorbable polymer can be blended with a more rigid, less rapidly degrading polymer to attain the qualities of rapid initial degradation of most of the structure while maintaining a rigid frame for longer periods of time.

Yet another alternative is to fabricate the bladder of degradable material. For instance, the balloon could be made of Vicryl® (Ethicon) or PDS®.

Self-deflating devices in accordance with this invention should be packaged and stored under drying conditions to prevent possible pre-mature degradation.

Having thus described the present invention with reference to particular embodiments, those skilled in the art to which it pertains may appreciate modifications and substitutions that do not depart from the spirit and scope of the invention as defined by the claims that follow.

We claim:

1. A self-inflating intragastric medical device comprising:
   1) an uninflated, ingestible, substantially liquid-impermeable balloon having an exterior surface and an interior surface, the interior surface bounding a lumen;
   2) an emissive substance enclosed within the balloon, wherein the emissive substance is a substance that liberates gas when contacted with a reactants;
   3) a vessel enclosed within the balloon and enclosing a space within the balloon separate from the lumen, wherein at least a portion of the vessel is fabricated of a gelatin that is soluble in at least one liquid selected from the group consisting of:
      1. water,
      2. organic acids that are liquid at room temperature, and
      3. solutions of mineral or organic acids;
   and wherein the vessel comprises a receptacle fabricated of the gelatin and having a mouth, further wherein the receptacle is attached at the mouth to a septum by a liquid-impermeable seal; and
   4) a self-sealing valve providing fluid communication into the vessel from outside the balloon, wherein the self-sealing valve is the septum.

2. The self-inflating intragastric device of claim 1 wherein the receptacle is attached to the septum by an adhesive.

3. The self-inflating intragastric device of claim 1 wherein the balloon comprises a bladder formed of non-self-sealing material having an opening, further wherein the opening is closed to passage of a liquid by the self-sealing valve.

4. The self-inflating intragastric device of claim 3 wherein the bladder is formed of a material selected from the group consisting of Dacron®, rubber, latex, silicone and nylon.

5. The self-inflating intragastric device of claim 3 wherein the self-sealing valve is positioned in the opening of the bladder and is held in the opening with a substantially liquid-impermeable seal.

6. The self-inflating intragastric device of claim 5 wherein the seal is effected by sealing means selected from the group consisting of partial melting, an adhesive substance and a clamp.

7. The self-inflating intragastric device of claim 6 wherein the seal is effected by a clamp and the clamp is a band encircling the open end of the bladder around the self-sealing valve.

8. The self-inflating intragastric device of claim 7 further comprising a rigid sleeve encircling the self-sealing valve and mediating the seal between the self-sealing valve and the bladder.

9. The self-inflating intragastric medical device of claim 7 wherein under conditions of use the band slowly erodes causing the liquid-impermeable seal between the self-sealing valve and the bladder to break after an approximately predetermined period of time resulting in deflation of the balloon.

10. The self-inflating intragastric medical device of claim 9 wherein the band is resorbable suture string.

11. The self-inflating intragastric medical device of claim 1 further comprising a container enclosing the balloon and sized to allow passage through the esophagus.

12. A kit comprising:
   1) the self-inflating intragastric medical device of claim 1 and
   2) a syringe.

13. The kit of claim 12 wherein the syringe is pre-filled with an activating liquid selected from the group consisting of water, organic acids that are liquid at room temperature, solutions of mineral acids, and solutions of organic acids.

14. The kit of claim 13 wherein the activating liquid is selected from the group consisting of a solution of citric acid, acetic acid, aqueous acetic acid and aqueous hydrochloric acid.

15. The kit of claim 14 wherein the activating liquid is comprised of a mixture of from about 25% to about 50% (v/v) acetic acid and from about 50% to about 75% (v/v) water.

16. The kit of claim 13 wherein the activating liquid is comprised of a mixture of about 33% acetic acid and about 67% (v/v) water.

17. The kit of claim 12 further comprising printed instructions describing how to orally administer the self-inflating intragastric medical device.

18. A self-inflating intragastric medical device comprising:
   1) an uninflated, ingestible, substantially liquid-impermeable balloon having an exterior surface and an interior surface, the interior surface bounding a lumen;
   2) an emissive substance enclosed within the balloon, wherein the emissive substance is a substance that liberates gas when contacted with a reactant;
   3) a vessel enclosed within the balloon and enclosing a space within the balloon separate from the lumen, wherein at least a portion of the vessel is fabricated of a gelatin that is soluble in at least one liquid selected from the group consisting of:

1. water,
2. organic acids that are liquid at room temperature, and
3. solutions of mineral or organic acids;

and wherein the vessel comprises a receptacle fabricated of the gelatin and having a mouth, further wherein the receptacle is attached at the mouth to a septum by a liquid-impermeable seal; and 4) a self-sealing valve providing fluid communication into the vessel from outside the balloon, wherein the self-sealing valve is the septum, and wherein the receptacle is attached to the septum by:
   1) moistening the mouth of the receptacle with water, thereby causing the gelatin proximate to the mouth to soften,
   2) contacting the mouth of the receptacle with the septum, and
   3) hardening the softened gelatin to form a liquid-impermeable seal between the septum and receptacle.

19. A self-inflating intragastric medical device comprising:
   1) an uninflated, ingestible, substantially liquid-impermeable balloon having an exterior surface and an interior surface, the interior surface bounding a lumen,
   2) an emissive substance enclosed within the balloon, wherein the emissive substance is a substance that liberates gas when contacted with a reactant,
   3) a vessel enclosed within the balloon and enclosing a space within the balloon separate from the lumen, wherein at least a portion of the vessel is fabricated of a material that is soluble in at least one liquid selected from the group consisting of
      1. water,
      2. organic acids that are liquid at room temperature, and
      3. solutions of mineral or organic acids, and
   4) a self-sealing valve providing fluid communication into the vessel from outside the balloon, wherein the self-sealing valve is a septum, and further comprising a reactant enclosed within the vessel and separated from the emissive substance by the vessel wall.

20. The self-inflating intragastric medical device of claim 19, wherein the reactant is in a solid state.

21. The self-inflating intragastric medical device of claim 19, wherein the reactant is in a liquid state.

22. The self-inflating intragastric medical device of claim 19, wherein the reactant is an acid.

* * * * *